US012263379B2

(12) United States Patent
Kunitz

(10) Patent No.: US 12,263,379 B2
(45) Date of Patent: Apr. 1, 2025

(54) SYSTEMS AND METHODS FOR DELIVERING A PERSONALIZED DOSE OF EXERCISE

(71) Applicant: FITBEAT AUSTRALIA PTY LTD, Rose Bay (AU)

(72) Inventor: Michael Vernon Kunitz, Rose Bay (AU)

(73) Assignee: FITBEAT AUSTRALIA PTY LTD, Rose Bay (AU)

( * ) Notice: Subject to any disclaimer, the term of this patent is extended or adjusted under 35 U.S.C. 154(b) by 696 days.

(21) Appl. No.: 17/437,104

(22) PCT Filed: Mar. 16, 2020

(86) PCT No.: PCT/AU2020/050249
§ 371 (c)(1),
(2) Date: Sep. 8, 2021

(87) PCT Pub. No.: WO2020/186297
PCT Pub. Date: Sep. 24, 2020

(65) Prior Publication Data
US 2022/0176202 A1 Jun. 9, 2022

(30) Foreign Application Priority Data
Mar. 15, 2019 (AU) ................................ 2019900855

(51) Int. Cl.
*A63B 24/00* (2006.01)
*A63B 71/06* (2006.01)

(52) U.S. Cl.
CPC ...... *A63B 24/0075* (2013.01); *A63B 24/0062* (2013.01); *A63B 71/0622* (2013.01);
(Continued)

(58) Field of Classification Search
CPC .............................. G09B 19/00; A63H 24/00
See application file for complete search history.

(56) References Cited

U.S. PATENT DOCUMENTS

| 2011/0281249 A1* | 11/2011 | Gammell | ............... G16H 10/20 434/247 |
| 2012/0040799 A1* | 2/2012 | Jaquish | .............. A63B 23/0355 482/9 |

(Continued)

OTHER PUBLICATIONS

Search Report for International Patent PCT/AU2020/050249, mailed Apr. 28, 2020.

*Primary Examiner* — Kurt Fernstrom
(74) *Attorney, Agent, or Firm* — FRESH IP PLC; Clifford D. Hyra; Aubrey Y. Chen

(57) ABSTRACT

Embodiments of the present disclosure provides a system for delivery of a personalised dose of exercise to subjects, comprising a computing device configured to obtain information pertaining to the subjects. The system further includes a fitness program determining device configured to: store information about the subjects; determine a personalised dose of exercise for a subject based on the information of the subject; and schedule the personalised dose of exercise to one or more exercise zones and points in time in a physical gym. The system furthermore includes an instruction device for providing personalised instructions to the subject based on the personalised dose of exercise at the points in time. The personalised instructions includes instructions for performing activities in the exercise zones, an order in which the activities to be performed in the exercise zones, and a workout sequence and a timing in which the exercise zones are to be completed.

20 Claims, 1 Drawing Sheet

(52) U.S. Cl.
CPC ............... *A63B 2024/0065* (2013.01); *A63B 2024/0068* (2013.01); *A63B 2024/0081* (2013.01)

(56) References Cited

U.S. PATENT DOCUMENTS

| | | | | |
|---|---|---|---|---|
| 2012/0122063 A1* | 5/2012 | Chen | ................ | G16H 20/30 434/247 |
| 2012/0196256 A1* | 8/2012 | Maeueler | ............... | G16H 20/30 434/247 |
| 2013/0143188 A1* | 6/2013 | Hong | ................ | A63B 24/0075 434/247 |
| 2014/0080108 A1* | 3/2014 | Zimmerman | .......... | G16H 20/30 434/247 |
| 2014/0212855 A1* | 7/2014 | Robinson | ............ | G09B 19/00 434/247 |
| 2014/0272855 A1* | 9/2014 | Maser | ................ | G11B 27/031 434/247 |
| 2015/0140532 A1* | 5/2015 | Whitney | .............. | G09B 19/003 434/247 |
| 2015/0220705 A1* | 8/2015 | Lin | ................ | G16H 20/30 434/247 |
| 2015/0364058 A1* | 12/2015 | Lagree | ............... | G09B 19/0038 434/257 |
| 2016/0074707 A1* | 3/2016 | Thorpe | .............. | G09B 19/0092 434/247 |
| 2016/0096075 A1* | 4/2016 | Leppänen | .......... | A63B 24/0075 434/247 |
| 2016/0144236 A1* | 5/2016 | Ko | ................ | G16H 20/30 434/247 |
| 2016/0151672 A1* | 6/2016 | Barnes | .................. | G06Q 30/02 434/247 |
| 2016/0163225 A1* | 6/2016 | Martens | ............... | A63B 21/072 434/247 |
| 2016/0239639 A1* | 8/2016 | Bernard-Paroly | .......................... | G09B 19/0038 |
| 2017/0007885 A1* | 1/2017 | Kerwin | .............. | G09B 19/0038 |
| 2017/0100636 A1 | 4/2017 | Umetsu et al. | | |
| 2017/0173394 A1 | 6/2017 | Rider | | |
| 2017/0216671 A1* | 8/2017 | Wisbey | ............... | A61B 5/02438 |
| 2018/0021658 A1* | 1/2018 | Samejima | ............. | A61B 5/681 434/255 |
| 2018/0214729 A1 | 8/2018 | Rubin et al. | | |
| 2018/0280782 A1* | 10/2018 | Lagree | ............... | A63B 71/0619 |
| 2020/0016457 A1* | 1/2020 | Ben-Chanoch | .... | A63B 24/0006 |

\* cited by examiner

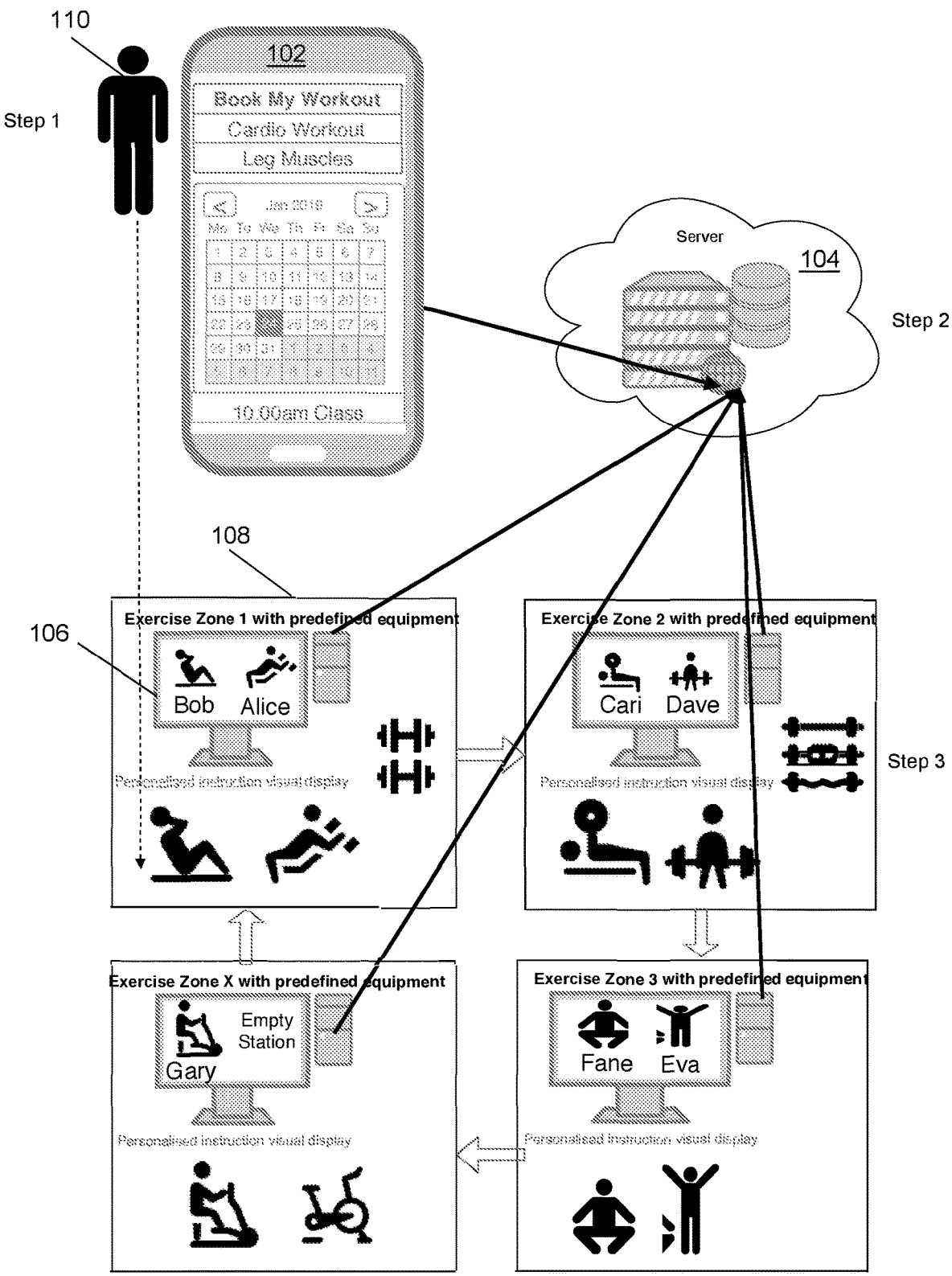

SYSTEMS AND METHODS FOR DELIVERING A PERSONALIZED DOSE OF EXERCISE

TECHNICAL FIELD OF THE INVENTION

The present disclosure relates to systems for delivering a personalized dose of exercise to a subject. In particular, the present disclosure relates to systems and methods for delivery of a personalized dose of exercise to one or more subjects, without the need for a personal trainer or a personal mobile device in the gym.

BACKGROUND

Any references to methods, apparatus or documents of the prior art are not to be taken as constituting any evidence or admission that they formed, or form part of the common general knowledge.

It would be attractive, practically and commercially, to be able to allow gym goers to train in a group or individual setting without personal trainers, but still have the benefit of personal guidance specific to their needs and desires. It would also be useful for gym goers to be able to see the guidance during the workout without relying on their own mobile device.

At present, those wanting personalized exercise experiences in a gym is generally limited to two options. The first option is paying for personal trainers that can design workouts based on the gym goers input and performance, and assist them during the workout. This is both expensive and not suited to everyone. The second option is carrying a mobile device around during the workout with an application running that provides personalized workouts, but this option is cumbersome and not a streamlined experience since: (1) the person should carry their mobile device with them and look at it constantly; (2) the gym equipment isn't laid out for the workout sequence on general workout applications; (3) and these applications cannot guarantee availability of gym equipment when the person gets there.

It is an object of the present invention to overcome or ameliorate the above discussed disadvantages of the prior art, or at least offer a useful alternative.

SUMMARY

An embodiment of the present disclosure provides a system for delivery of a personalized dose of exercise to one or more subjects, comprising: a computing device configured to obtain information pertaining to the one or more subjects. The system further includes a fitness program determining device configured to: store information about the one or more subjects; determine a personalized dose of exercise for a subject of the one or more subjects based on obtained information of the subject and pre-stored information about exercises from a database of the system; and schedule the personalized dose of exercise to one or more exercise zones and points in time in a physical gym comprising the one or more exercise zones. The system furthermore includes an instruction device configured to provide one or more personalized instructions to the subject based on the determined personalized dose of exercise at the points in time scheduled by the fitness program determining device. The one or more personalised instructions includes at least one of instructions for performing one or more activities in the one or more exercise zones, an order in which the one or more activities to be performed in the one or more exercise zones, and a workout sequence and a timing in which the one or more exercise zones are to be completed to deliver the personalized dose of exercise for the subject.

The system may determine and provide the personalized dose of exercise to the subject. By "personalised" is meant that the dose of exercise is designed to fulfil a set of criteria determined by the needs, desires preferences, existing conditions/injuries/fitness level, goals and/or training program etc. of the subject.

According to an aspect of the present disclosure, for each of the one or more subjects, the information may include at least one of an age, a gender, a desired general fitness goal, a desired workout style for said dose of exercise, a desired target area for said dose of exercise, a desired time, date, duration of dose of exercise and/or location for said dose of exercise, a details of one or more previous doses of exercise delivered to said subject, data relating to a parameter selected from the group consisting of weight, heart rate, blood pressure, percentage body fat, BMI, blood glucose level, ECG, respiratory rate, muscle mass, steps, energy expenditure, energy intensity, and so forth.

According to another aspect of the present disclosure, the fitness program determining device is further configured to determine a personalized smart meal plan for the subject based on the information of the subject and pre-stored information about smart meal plans from the database. The smart meal plans may be customized for each subject, taking into account various details on each subject as well as their long-term fitness goal, preferences etc.

According to another aspect of the present disclosure, the personalized dose of exercise for the subject may include at least one of a plurality of exercises to be performed by the subject in each of the one or more exercise zones.

According to another aspect of the present disclosure, the fitness program determining device is configured to schedule the personalized dose of exercise to one or more exercise zones and points in time in a physical gym comprising the one or more exercise zones in a manner that optimises the timing and physical locations of a subject's individual workout in a gym; avoids gym congestion by ensuring that there are no more than a maximum number of subjects at an exercise zone at any single time; and ensures that the capacity of the gym is utilized most effectively allowing the maximum number of subjects to train at any timing without being in each other's way; and optionally enables workouts from a multitude of subjects to be scheduled simultaneously to create a time-synchronised, gym class-based group training environment.

According to another aspect of the present disclosure, the system also includes a reporting device configured to: receive personalized statistics information about the subject from one or more personal information capturing devices; create a smart report for the subject by measuring and/or interpreting the subject's analytics in relation to the subject's starting analytics and based on the personalized statistics information, information about the workouts, user inputs, inputs from the computing device, statistics derived from body scans of the subject, changing statistics measured during the workout according to the personalized dose of exercise and compared to the statistics prior to the workout and after the workout, and long-term fitness goal of the subject; and present a smart report to the subject, wherein the smart report is displayed on the computing device.

According to another aspect of the present disclosure, the subject may be a part of a group comprising the one or more subjects.

In an embodiment, the subject is a person performing one or more exercises in each of the one or more exercise zones as per his/her personalized dose of exercise by being a part of the group.

According to another aspect of the present disclosure, the fitness program determining device is further configured to determine a group personalized dose of exercise for the group and individual personalized dose of exercise for each of the one or more subjects of the group based on the information of the one or more subjects.

According to another aspect of the present disclosure, the computing device is configured to obtain additional information for each subject of the one or more subjects during the personalized dose of exercise as performed by each subject. Further, the computing device sends the additional information to the fitness program determining device. The fitness program determining device may store the additional information.

According to another aspect of the present disclosure, the fitness program determining device may also be configured to modify the personalized dose of exercise being delivered to each subject in response to the additional information obtained during the personalized dose of exercise.

The non-limiting examples of the computing device may include at least one of a mobile device, a desktop computer in communication, a laptop, a smart television, a smart phone, a tablet computer, a fitness tracker, a body composition analyzer, a personal monitoring device, a power output monitoring device connected to a piece of equipment in one or exercise zones, wherein the power output monitoring device. The computing device may be in communication with the fitness program determining device.

According to another aspect of the present disclosure, the fitness program determining device may be a server. Further, the fitness program determining device may be in communication with at least one of the instruction device and the computing device.

According to another aspect of the present disclosure, the instruction device may include an audio/video display device located in proximity of the exercise zones. Further, each of the one or more exercise zones may include a separate instruction device comprising a separate audio/video display device for each of the one or more exercise zones.

In some embodiments, the instruction device may store a plurality of exercises that may not be subject-specific. According to another aspect of the present disclosure, the instruction device may function in an offline mode when it is not connected to the fitness program determining device. In this offline mode, the instruction device can determine and show its own selection of exercises from the pre-stored plurality of exercises that is not-subject specific.

According to yet another aspect of the present disclosure, an exercise zone of the one or more exercise zones accommodates two or more subjects of the one or more subjects performing an activity simultaneously. Further, the instruction device may be configured to provide personalized instructions for the two or more subjects in the same exercise zone simultaneously to perform a different activity based on a personalized dose of exercise of the two or more subjects.

Another embodiment of the present disclosure provides a method for delivering a personalized dose of exercise to one or more subjects, comprising: obtaining, by a computing device, information pertaining to the one or more subjects; determining, by a fitness program determining device, a personalized dose of exercise for a subject of the one or more subjects based on the information of the subject received from the computing device. The method also includes storing, by the fitness program determining device, information pertaining to the one or more subjects. The method further includes scheduling, by the fitness program determining device, the personalized dose of exercise to one or more exercise zones and points in time in a physical gym comprising the one or more exercise zones. The method further includes providing, by an instruction device, one or more personalized instructions to the subject based on the determined personalized dose of exercise at the points in time scheduled by the fitness program determining device. The one or more personalized instructions may include instructions for performing one or more activities in at least one exercise zone of one or more exercise zones, an order in which the one or more activities to be performed in the one or more exercise zones, and a workout sequence and a timing in which the one or more exercise zones are to be completed to deliver the personalized dose of exercise for the subject, and so forth.

According to another aspect of the present disclosure, the method may also include determining, by the fitness program determining device, a personalised smart meal plan for the subject based on the information of the subject.

According to another aspect of the present disclosure, the method may also include determining, by the fitness program determining device, a group personalized dose of exercise for the group and individual personalized dose of exercise for each of the one or more subjects of the group based on the information of the one or more subjects.

The method may also include: obtaining, by the computing device, additional information for each subject of the one or more subjects during the personalised dose of exercise as performed by each subject; storing, by the fitness program determining device, the additional information; and modifying, by the fitness program determining device, the personalized dose of exercise being delivered to each subject in response to the additional information obtained during the personalized dose of exercise.

In some embodiments, an exercise zone of the one or more exercise zones can accommodate two or more subjects of the one or more subjects performing an activity simultaneously.

The method may also include providing, by the instruction device, instructions for the two or more subjects in the same exercise zone simultaneously to perform a different activity based on a personalized dose of exercise of the two or more subjects.

The method may also include receiving, by a reporting device, personalised statistics information about the subject from one or more personal information capturing devices; creating, by the reporting device, a smart report for the subject by measuring and/or interpreting the subject's analytics in relation to the subject's starting analytics and based on the personalized statistics information, information about the workouts, user inputs, inputs from the computing device, statistics derived from body scans of the subject, changing statistics measured during the workout according to the personalized dose of exercise and compared to the statistics prior to the workout and after the workout, and long-term fitness goal of the subject; and presenting, by the reporting device, a smart report to the subject, wherein the smart report is displayed on the computing device.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. The invention will be more particularly described in conjunction with the following drawings wherein:

FIG. 1 shows an exemplary system for delivering a personalized dose of exercise to one or more subjects, accorsing to at least one embodiment.

DETAILED DESCRIPTION

Preferred features, embodiments and variations of the invention may be discerned from the following detailed description which provides sufficient information for those skilled in the art to perform the invention. The detailed description is not to be regarded as limiting the scope of the preceding summary of the invention in any way.

Specific embodiments of the present invention are described, by way of example only, with reference to the accompanying drawings, in which FIG. 1 shows an exemplary system 100 for delivering a personalized dose of exercise to one or more subjects, in accordance with an embodiment of the present disclosure may function.

As shown, the system 100 primarily includes a computing device 102, a fitness program determining device 104, and an instruction device 106 located in each exercise zone 108 of one or more exercise zones. Further, each exercise zone 108 of the one or more exercise zones includes pre-defined set of equipment. The set of equipment in each of the one or more exercise zones may be pre-defined by based on a setting order automatically determined by the fitness program determining device 104 (i.e. a server). In some embodiments, the fitness program determining device 104 may determine the setting order based on an input from a user such as, an administrator of the system 100. Further, the instruction device 106 may be installed in each exercise zone 108 of one or more exercise zones. A subject 110 can access the system 100 on the computing device 102. The subject 110 may be any human wishing to exercise with instruction, that is in possession of, or has access to, a means of providing the required information for the system 100. The system 100 may determine and provide a personalized dose of exercise to the subject 110. By "personalised" is meant that the dose of exercise is designed to fulfil a set of criteria determined by the needs, desires preferences, existing conditions/injuries/fitness level, goals and/or training program etc. of the subject 110.

The computing device 102 is configured to obtain information pertaining to the one or more subjects such as the subject 110. Examples of the computing device 102 may include, but are not limited to, a mobile device, a desktop computer in communication, a laptop, a smart television, a smart phone, a tablet computer, a fitness tracker, a personal monitoring device, a power output monitoring device connected to a piece of equipment in one or exercise zones, wherein the power output monitoring device. The computing device 102 may be in communication with the fitness program determining device 104. For each of the one or more subjects, the information may include such as, but not limited to, at least one of an age, a gender, a desired workout style, a desired general fitness goal for said dose of exercise, historical information (past personal dose of exercise for the subject, medical information, etc.) of the subject 110, a desired target area for said dose of exercise, a desired time, date, duration of dose of exercise and/or location for said dose of exercise, a details of one or more previous doses of exercise delivered to the subject 110, data relating to a parameter selected from the group consisting of weight, heart rate, blood pressure, percentage body fat, BMI, blood glucose level, ECG, respiratory rate, muscle mass, steps, energy expenditure and energy intensity.

In some embodiments, the computing device 102 may obtain information such as, but not limited to, an age and gender of the subject. In some embodiments, the information of the subject 110 (hereinafter, information of the subject 110 may also be referred as subject information without change in its meaning) obtained may also include the subject's desired workout style, desired target area, and general fitness goals. Non limiting examples of general fitness goals may include getting lean, building muscle, getting fit, and getting strong. Non limiting examples of desired workout styles may include cardio (aerobic and/or anaerobic), resistance (such as weight training), flexibility, weight loss, active recovery, balance, boxing, circuit, high-intensity interval training, cross-training, stretching, rehabilitation, tapering, endurance and combinations thereof. The target area may be any area of the subject's body that they wish to focus on during a particular dose of exercise. For example, typical target areas may be legs (upper, lower, calves, thighs, inner thighs etc.), arms, back (lower, upper), abs (core), grip strength, shoulders, chest, gluteus muscles and combinations thereof. The subject 110 may nominate more than one workout style and/or more than one target area according to desired outcomes. Alternatively, the subject 110 may simply nominate their general system goal without nominating a specific workout style or target area.

The fitness program determining device 104 may be configured to receive the information pertaining to the one or more subjects from the computing device 102. In some embodiments, the fitness program determining device 104 may store the information pertaining to the one or more subjects. The fitness program determining device 104 is also configured to determine a personalized dose of exercise for a subject, such as the subject 110, of the one or more subjects based on information of the subject 110 and pre-stored information related to exercises from a database. In some embodiments, the database may be an integral part of the fitness program determining device 104. Alternatively, the database may be a remote database in communication with the fitness program determining device 104. Further, the fitness program determining device 104 is also configured to schedule the personalized dose of exercise to one or more exercise zones and points in time in a physical gym comprising the one or more exercise zones. The fitness program determining device 104 is also configured to schedule the personalized dose of exercise to one or more exercise zones and points in time in a physical gym in a manner that optimizes the timing and physical locations of a subject's individual workout in a gym to streamline the workout; avoids gym zone congestion by ensuring that there are no more than the maximum amount of subjects at a zone at any single time; and ensures that the capacity of the gym is utilized most effectively so as to allow the maximum amount of subjects to train at any timing without being in each other's way, and may optionally enables workouts from a multitude of subjects to be scheduled simultaneously to create a time-synchronized, gym class-based group training environment.

Furthermore, the fitness program determining device 104 is also configured to determine a personalized smart meal plan based on the information of the subject 110 and pre-stored information related to smart meal plans from the database.

In an embodiment, the fitness program determining device 104 may be a server. Further, the fitness program determining device 104 may include a database for storing the information (or additional information) about the one or more subjects including the subject 110. Further, the fitness program determining device 104 may be in communication with at least one of the instruction device 106 and the computing device 102. The personalized dose of exercise for the subject 110 (or for each of the one or more subjects) may include a plurality of exercises to be performed by the subject 110 in each of the one or more exercise zones.

In some embodiments, the subject 110 is part of a group comprising the one or more subjects. In such embodiments, the fitness program determining device 104 is further configured to determine a group personalized dose of exercise for the group and/or individual personalized dose of exercise for each of the one or more subjects of the group based on the information of the one or more subjects.

The instruction device 106 is configured to provide one or more personalised instructions to the subject 110 based on the determined personalized dose of exercise (that is determined by the fitness program determining device 104). The instruction device 106 may be an instruction presenting device like a display screen, configured to receive personalized dose of exercise of the subject 110 from the device 104 and present to the subject 110. The one or more personalized instructions may include, instructions such as, but not limited to, instructions for performing one or more activities in at least one exercise zone, such as the exercise zone 108, of one or more exercise zones and an order related instruction in which the one or more activities and the one or more exercise zones are to be completed to deliver the personalized dose of exercise for the subject 110. The instruction device 106 may include an audio/video display device located in proximity of the one or more exercise zones. Further, each of the one or more exercise zones may include a separate instruction device 106 including a separate audio/video display device for each of the one or more exercise zone.

In some embodiments, the instruction device 106 may store a plurality of exercises that may not be subject-specific. In some embodiments, the instruction device 106 may also configured to operate when not connected to the fitness program determining device 104. According to another aspect of the present disclosure, the instruction device 106 may function in an offline mode when it is not connected to the fitness program determining device. In this offline mode, the instruction device 106 may determine and show its own selection of exercises from the pre-stored plurality of exercises that is not-subject specific.

In some embodiments, the instruction device 106 may be in communication with the computing device 102. In such embodiments, the instruction device 106 may receive the subject information from the computing device 102. Further, the one or more functions of the fitness program determining device 104 may be performed by the instruction device 104. In some embodiments, the device 104 may be embedded within the instruction device 106. In some embodiments, the computing device 102 may be configured to perform one or more functions of the device 104.

In some embodiments, the computing device 102 is also configured to obtain additional information for each subject, such as the subject 110, of the one or more subjects during the personalized dose of exercise as performed by each subject. In some embodiments, the fitness program determining device 104 is also configured to modify the personalized dose of exercise being delivered to each subject in response to the additional information obtained during the personalized dose of exercise. In some embodiments, the fitness program determining device 104 may store the additional information for each subject.

In some embodiments, an exercise zone like the zone 108 of the one or more exercise zones accommodates two or more subjects of the one or more subjects performing an activity simultaneously, further wherein the instruction device is configured to provide instructions for the two or more subjects in the same exercise zone simultaneously to perform a different activity based on a personalized dose of exercise of the two or more subjects.

In an exemplary scenario, once a member (or the subject 110) has selected a long-term fitness goal, then the member may simply book a timeslot by using the system 100, and then the fitness program determining device 104 (may also be referred as a Smart PT) calculates a workout for the member, which forms parts of an overall workout program for each member (such as the subject 110). So, for e.g., if 5 bookings are made by a member, and booking #2 is cancelled, then the workout settings for booking #2 are automatically shifted over to booking #3 by the device 104. In some embodiments, the system 100 enables the member to self-manage his/her workout program. For example, each time the member books a workout, he/she can simply accept the workout settings, or they can manually override the settings for each and every workout, thereby effectively self-managing their workout program.

At step 1, the subject 110 accesses the system 100 for delivering a personalised dose of exercise to one or more subjects is performed by accessing the system on the computing device 102. In some embodiments, the subject 110 (hereinafter may also be referred as a user) accesses the system 100 via a mobile application installed on the computing device 102 that can be a mobile phone. Alternatively, the subject 110 may access the system 100 by entering a network address, a link, or a uniform resource locator (URL) on a browsing application on the computing device 102. The subject 110 may enter information such as, but not limited to, a general fitness goal, an age, a gender, a preference, a weight, a height, and so forth, on the computing device 102. In some embodiments, the subject 110 may select a personal workout (wherein the workout is the "dose of exercise") preferences (including but not exclusive to level, muscle groups, gender). This can be for a single workout, or a single day of general preferences etc.

At step 2, the computing device 102 communicates with the fitness program determining device 104 i.e. the server and, based on the information obtained from the subject 110, checks the availability of workouts at a gym location. The computing device 102 may retrieve the availability schedule from the fitness program determining device 104 and the subject 110 then may book a workout by selecting an available gym location, date, time and duration of the workout. The workout may be based on a personalized dose of exercise for the subject 110, and the workout may include exercises scheduled to specific zones of the one or more exercise zones at specific points in time.

Further, the fitness program determining device 104 may receive and store the information of the subject 110 (or the that of the one or more subjects) from the computing device 102. Further, the fitness program determining device 104 may store a detailed schedule of each gym's exercise zones, and which subjects of the one or more subjects will be at each equipment zone at each point in time. When the subject requests availability for a workout or books, the fitness program determining device 104 may calculate if there is availability in a series of consecutive exercise zones to create a full workout and if the subject's workout can move through the exercise zones in sequence without conflicting with other subjects' workouts. The device 104 while availability/scheduling calculation may be aware that each exercise zone can have more than one slot and can potentially cater to multiple subjects. When the subject books, the subject's workout (a series of consecutive exercise zones in time sequence) is committed to a schedule database of the device 104 to finalize a workout booking.

The fitness program determining device 104 may use all of the subject information obtained, in conjunction with the available information in relation to the gyms stored on the fitness program determining device 104, to calculate and enforce a micro-scheduling schedule that prevents any conflicting or overlapping workouts. This schedule is changed in real-time when a change occurs, such as, for example, when a subject modifies their dose of exercise during the dose of exercise, which may open or close the availability of an exercise zone and/or activity for another subject at a particular time.

The fitness program determining device 104 may provide a personalized dose for the subject 110 based on information of the subject 110 received from the computing device 102.

In step 3, the instruction device 106 including an audio/video device in each exercise zone, which is a monitor with a computer connected to the device 104 may retrieve the workout schedule, personalized activity instructions, subject information and more from the device 104 and present the same to the subject 110 at the right time and place. For example, if subjects like Bob and Alice are in the exercise zone 108 then the instruction device 106 displays one or more exercises separately for the Bob and Alice. This way, though the Bob and Alice are doing the exercises together but still the instruction device is displaying different exercise for them to perform as per their respective personalized dose of exercise determined by the device 104.

On the device 104 i.e. the server, when the instruction device 106 request a schedule, the server returns applicable subject information and personalised activity instructions for that exercise zone and time. The server achieves this by maintaining a database of activities and runs an algorithm that selects the most applicable workout activities based on subject preferences, exercise zone equipment, time and other factors to determine the most applicable activities. This algorithm also caters for manual overrides.

The subject can enter the gym and start a workout without accessing the App at the booked time. They will then find their personal information and workout instructions already displayed on a visual display in proximity to their first scheduled exercise zone, without applying any settings or carrying any device. They will be guided through the consecutive exercise zones by the visual displays.

As can be seen in FIG. 1, during step 3, there are multiple subjects using a selection of exercise zones in unison, and are completing a personalized workout by following the instructions of the visual displays.

During this step 3, the subject may also optionally register a personal monitoring device using the identification details of his/her personal monitoring device through the system 100 on the computing device 102 and/or gym staff may register power output monitoring devices in communication with the fitness program determining device 104 for equipment used in specific exercise zones.

In some embodiments, the subject information obtained by the computing device 102 is stored in a network device such as a storage server. The storage server may be same or different than the fitness program determining device 104 that is used for determining the personalized dose of exercise for the subject 110. The server or the fitness program determining device 104 may store details of a multitude of possible venues, available time slots, available exercise zones, pieces of equipment and accompanying activities, as well as information on the appropriateness of each activity, exercise zone and/or piece of equipment indexed or scored against a multitude of parameters related to any subject information obtained.

For example, the fitness program determining device 104 or the server may include a multitude of activities suitable for a 56-year old male subject wishing to do a balance workout targeting abs, wherein the subject has previously completed 6 previous doses of exercise and desires variation in every dose, and would like to maintain a particular heart rate during the dose of exercise.

The computing device 102 may gather subject metrics/measurements in real-time, which is stored in the storage server or the device 104, and may be presented on the instruction device 106 in the one or more exercise zones.

The system 100 may allow the one or more subjects to exercise in a gym environment, or in any location with an appropriate means of providing instructions and at least one exercise zone with pre-defined pieces of equipment, in accordance with a personalized dose of exercise, whilst allowing the subject the flexibility of choosing whether to exercise alone, or in a group. Further, each subject in the group may have a personalized dose of exercise being generated by the fitness program determining device based on information of each subject.

In embodiments, the system 100 (or the computing device of the system 100) may also obtain and store information pertaining to the subject's desired time, date, duration of a dose of exercise and/or location for said dose of exercise and the means of determining a personalized dose of exercise for each subject may then utilize this information to determine a selection of options for where and when the subject may complete the dose of exercise. For example, the system 100 may be connected to a number of different commercial gyms or studios with different availability for different times/days/duration for the dose of exercise and/or different workout styles and/or for numbers of subjects similar to the subject 110.

An example of the subject information that may be obtained and stored for a particular subject is: male; 38; cardio workout; legs; Tuesday; 7 pm; 45 min dose; Bondi. In another example, the subject information that may be obtained and stored is: female; 21; weight loss and rehabilitation; lower back; Sunday; Sydney.

The system 100 or the computing device 102 may also obtain and store additional information of previous and subsequent doses of exercise delivered to a particular subject on at least one of the fitness program determining device 104 or the storage server. This additional information may include details about the performance of the subject 110 during any dose of exercise. It would be understood that additional information stored and obtained in relation to previous doses of exercise can be informative when determining subsequent personalised doses of exercise and can assist with the tracking of progress for the subject 110 in the context of his/her desired goals. The information of previous doses of exercise may also be used to ensure there is variation and/or consistency in subsequent doses of exercise (depending on the subject's desire for variation or consistency).

The system 100 may also obtain and store subject information relating to a parameter selected from the group consisting of weight, heart rate, blood pressure, percentage body fat, BMI, blood glucose level, ECG, respiratory rate, muscle mass, steps, energy expenditure and energy intensity, and the system may obtain this information from the subject at any time. For example, the subject 110 may provide this information when providing their age and gender, or the information may be obtained from the subject 110 during a dose of exercise, or the information may be obtained from the subject 110 sporadically if and when the information becomes available to the subject 110 through, for example, a body composition analysis.

In some embodiments, this information obtained from the subject 110 may be used by the device 104 to further refine the dose of exercise based on the overall health of the subject 110 in the context of their desired outcomes, and/or the performance of the subject 110 during a dose of exercise. The additional information of the subject 110 obtained may also be used to further refine the personalized dose of exercise for the subject 110 during the subject 110 is performing the personalized dose of exercise in real time. For example, in some embodiments, the system 100 obtains information about the subject's heart rate during the dose and, in the context of a desired/acceptable heart rate, modifies the instructions for the dose in real-time to maintain, reduce or increase the heart rate of the subject 110.

The computing device 102 may allow the subject 110 to refine or update the subject information during a personalized dose of exercise to modify the personalized dose of exercise based on, for example, preferences, changes in circumstances or issues that may arise during the personalized dose of exercise. For example, the subject 110 may injure themselves, need to complete the personalized dose of exercise earlier, or find they are missing a piece of required personal gear/equipment to complete the instructed activity in one or more exercise zone. This information obtained from the subject 110 during the dose of exercise may be used by the means of determining a personalized dose of exercise to further refine the dose of exercise and modify the instructions provided to, for example, modify activity to perform an exercise to avoid an injured area, reduce the duration of the dose of exercise, or substitute an activity for one that does not require the personal gear/equipment that the subject 110 is missing.

The system 100 may obtain information of the subject 110 in many ways. In some embodiments, the subject 110 may input (via voice or text or gesture) the information on the computing device 102 a mobile device or a desktop computer that is in communication with a server that stores the information. The subject 110 may also input information that can be obtained from a fitness and/or health assessment or body composition analysis (such as BMI, body fat percentage, muscle mass, etc.), and this may be updated in the device 104 (or the storage server) as it changes for said subject 110.

In some embodiments, the system 100 may determine the personalized dose of exercise based on the obtained information, pre-stored exercise information, and historical information of the subject 110.

In other embodiments, information pertaining to the subject 110 (or multiple subjects) may also be obtained by a personal monitoring device that is also in communication with the device 104 or the storage server, where the information is stored. Non-limiting examples of personal monitoring devices that may be used to obtain information in the system of the present invention include blood glucose monitors, pedometers and movement/GPS trackers that measure distance travelled (which may also convert to energy expenditure), heart monitors, mobile EKG monitors, wireless blood pressure monitors and/or EEG sensors. In some embodiments, the device 104 and the storage server are in communication with each other.

In some embodiments, the information of the subject 110 may also be obtained from one or more power output monitoring devices connected to piece of exercising equipment in the exercise zones, which are in communication with the device 104 and/or the storage server, where the information is stored. Examples of these power output monitoring devices include devices connected to rowers, stationary bicycles, stair mills, treadmills, ellipticals, skiergs and/or airdynes. It would be understood that the power output monitoring devices associated with such equipment may be used to obtain information relating to energy expenditure and energy intensity, as well as the overall performance of the subject 110 during the personalized dose of exercise for the subject 110.

The information obtained from personal monitoring devices and power output monitoring devices during a personalized dose of exercise may be used by the fitness program determining device 104 in the determination of a subsequent dose of exercise for the subject 110. For example, in some embodiments, the dose of exercise may include an exercise zone with a stationary bicycle comprising a means of measuring distance travelled, which is in communication with the server, and the information obtained from the bicycle may be used to increase the distance to be travelled in a subsequent dose of exercise to encourage improvement.

The information obtained from personal monitoring devices and power output monitoring devices may also be used by the device 104 during the dose of exercise to modify the dose of exercise. For example, in some embodiments, the dose of exercise may include an exercise zone with a treadmill comprising a means of measuring distance travelled and incline, which is in communication with the server, and the information obtained from the treadmill may be used to increase or decrease the intensity of the workout. In other embodiments of the invention, the system 100 (or the device 104) obtains information about the subject's heart rate when performing each activity during the dose exercise and, in the context of a desired heart rate and calculated energy expenditure, modifies the instructions for the dose in real-time to maintain, reduce or increase the energy expenditure of the subject 110.

The information obtained from the personal monitoring devices and power output monitoring devices in communication with the device 104, as well as any additional information obtained from the subject 110 by any other means, would be stored on the device 104 and be available for review and perusal by the subject 110 at any time, generally via the same means used by the subject 110 to provide at least their age and gender (i.e. their mobile device).

In an embodiment, the system 100 also includes a reporting device configured to: receive personalized statistics information about the subject from one or more personal information capturing devices; create a smart report for the subject by measuring and/or interpreting the subject's analytics in relation to the subject's starting analytics and based on the personalized statistics information, information about the workouts, user inputs, inputs from the computing device, statistics derived from body scans of the subject, changing statistics measured during the workout according to the personalized dose of exercise and compared to the statistics prior to the workout and after the workout, and long-term fitness goal of the subject; present a smart report to the subject, wherein the smart report is displayed on the computing device. In some embodiments, the one or more functions of the reporting device may be done by the computing device 102. In other embodiments, the one or more functions such as the smart report creation function of the reporting device may be performed by the fitness program determining device 104.

In some embodiments, the statistics may be derived from body scans of the subject 110 ran outside of the workouts, and may include metrics measured during the workouts and calculations done after the workouts, information about the workouts, and also inputs of the subject 110. Further, the reporting device may work with the other devices of the system 100, external computing devices and information storing device to calculate personalized statistics for the subject 110.

In some embodiments, the system 100 or the reporting device of the system 100 may use artificial intelligence for interpreting members' monthly body scans, heart rate monitor reports, and other smart reports.

In some embodiments of the present disclosure, the reporting device, may be one and the same as the computing device 104 and may be configured to show information about previous workouts, smart meal plans, and performance statistics.

The system 100 of the present disclosure is designed for use by more than one subject 110 at a time, in that each exercise zone may be used by more than one subject 110 during their dose of exercise. Alternatively, the system 110 may be used by one subject at time.

The system 110 of the present disclosure, may be utilized to deliver a personalized dose of exercise via either allowing for a plurality of activities to be performed in a single exercise zone, or allowing for a plurality of activities to be performed in a plurality of exercise zones, or allowing a single activity to be performed in a plurality of exercise zones, and combination thereof. It would be understood that a particular dose of exercise would not need to utilize all of the exercise zones, nor would the subject 110 may need to perform all of the activities in any given exercise zone.

Further, the one or more subjects may complete a personalized dose of exercise, in part, by traversing a selection of the exercise zones in a particular order and at specific times in accordance with the provided instructions. In other embodiments, the subjects may complete a personalized dose of exercise, in part, by performing a selection of activities in a particular order in an exercise zone in accordance with the provided instructions. In further embodiments, the subjects may complete a personalized dose of exercise, in part, by traversing a selection of the exercise zones in a particular order, wherein the each of the one or more subjects performs a selection of activities in a particular order in one or more exercise zones, and a single activity in one or more exercise zones, in accordance with the provided instructions via the instruction device 106.

In some embodiments, the exercise zones can accommodate two or more subjects simultaneously, and when the two or more subjects are in a particular exercise zones, they may be instructed to perform the same activity or a different activity, for a different duration or the same duration, and at a different intensity or the same intensity etc depending on the information obtained for each subject. It would be understood that for each exercise zone with particular pieces of equipment, there would be a plurality of activities available in the server database to form part of each subject's dose of exercise. For example, in exercise zone 2, Cari and Dave are the subjects performing two different activities (exercises) as displayed on the instruction device 106.

In the present invention, the instruction device 106 may provide instructions for each subject at least in relation to the exercise zone they are to perform an activity, the order in which they are to complete the exercise zones and/or activities. The instructions are provided by a means that is different to the means of obtaining the subject information, and the means of providing the instructions is generally independent of any objects or equipment the subject 110 requires or owns, and generally the subject 110 does not need to physically interact with the means of providing the instructions. This means the computing device 102 and the instruction device 106 are different devices. For example, if the subject information is obtained by a mobile device, this mobile device is not required for the provision of the instructions. In general, the means of providing the instructions is provided by, and permanently resides in, the venue where the dose of exercise is to be completed.

The provision of the instructions may commence automatically in accordance with desired time, date and/or venue information obtained from the subject 110, or the provision of the instructions may require a check-in or trigger for commencement to ensure the subject 110 is present. The instructions may also define the duration of the activity, the intensity of the activity, how to use the piece of equipment in the exercise zone, when to move to the next exercise zone and/or activity, when to rest etc. The instructions may also display information obtained from the subject 110 from a personal monitoring device and/or power output monitoring device in communication with the server during a dose of exercise, as well as providing information on any changes being made to the dose of exercise as the changes are made.

In some embodiments, the instruction device 106 for each subject to perform an activity is an audio/visual display device (i.e. the instruction device 106) in proximity of the exercise zones, and the means is in communication with the server. By proximity is meant that the subject 110 can see the audio/visual display device from the exercise zones, and generally while the proscribed activity is being performed. There may not be an audio/visual display device in communication with the device 104 or the storage server in proximity to every exercise zone, but in some embodiments of the present disclosure, there is a separate audio/visual display device for each exercise zone. The instructions provided by the audio/visual display device may be in the form of, for example, figures or diagrams, an avatar or written instructions, videos, audio clips or combinations thereof.

The system 100 is configured to constantly learn from member behaviour, and may use machine learning to constantly improve not only the individual subject's workouts, but that of the group of subjects too.

In compliance with the statute, the invention has been described in language more or less specific to structural or methodical features. The term "comprises" and its variations, such as "comprising" and "comprised of" is used throughout in an inclusive sense and not to the exclusion of any additional features. It is to be understood that the invention is not limited to specific features shown or described since the means herein described comprises preferred forms of putting the invention into effect. The invention is, therefore, claimed in any of its forms or modifications within the proper scope of the appended claims appropriately interpreted by those skilled in the art.

Any embodiment of the invention is meant to be illustrative only and is not meant to be limiting to the invention. Therefore, it should be appreciated that various other changes and modifications can be made to any embodiment described without departing from the spirit and scope of the invention.

What is claimed is:

1. A system for delivering a personalized dose of exercise to one or more subjects, comprising:
   a computing device configured to obtain information pertaining to the one or more subjects;
   a fitness program determining device communicably coupled to the computing device, the fitness program determining device configured to:
      determine a personalized dose of exercise for a subject of the one or more subjects based on the information of the subject received from the computing device and pre-stored information related to exercises from a database of the system;
      store information pertaining to the one or more subjects; and
      schedule the personalized dose of exercise to one or more exercise zones and points in time in a physical gym comprising the one or more exercise zones; and
   an instruction device communicably coupled to both the fitness program determining device and the computing device, the instruction device comprising an audio/video display device located in proximity to the one or more exercise zones,
   wherein, in each of the one or more exercise zones, a separate instruction device comprising a separate audio/video display device is installed,
   wherein the instruction device is configured to provide one or more personalized instructions to the subject based on the determined personalized dose of exercise at the points in time determined and scheduled by the fitness program determining device,
   wherein the one or more personalized instructions comprises at least one of:
      instructions for performing one or more activities in at least one exercise zone of one or more exercise zones,
      an order in which the one or more activities to be performed in the one or more exercise zones, and
      a workout sequence and a timing in which the one or more exercise zones are to be completed to deliver the personalized dose of exercise for the subject,
   wherein the one or more subjects comprises two or more subjects, and wherein each of the one or more exercise zones accommodates the two or more subjects performing an activity simultaneously,
   wherein the instruction device is configured to provide instructions to the two or more subjects when the two or more subjects are in a same exercise zone of the one or more exercise zones,
   wherein the instructions simultaneously instruct the two or more subjects to perform a different personalized exercise activity.

2. The system of claim 1, wherein for each of the one or more subjects, the information is selected from the group consisting of: an age, a gender, a desired general fitness goal, a desired workout style for the dose of exercise, a desired target area for the dose of exercise, a desired time, date, duration of dose of exercise and/or location for the dose of exercise, a details of one or more previous doses of exercise delivered to the subject, data relating to a parameter selected from the group consisting of weight, heart rate, blood pressure, percentage body fat, BMI, blood glucose level, ECG, respiratory rate, muscle mass, steps, energy expenditure, energy intensity, and combinations thereof.

3. The system of claim 2, wherein the fitness program determining device configured to determine a personalized smart meal plan for the subject based on the information of the subject and pre-stored information related to smart meal plans from the database.

4. The system of claim 3, wherein the personalized dose of exercise for the subject comprises a plurality of exercises to be performed by the subject in each of the one or more exercise zones.

5. The system of claim 4, wherein the subject is part of a group comprising the one or more subjects.

6. The system of claim 5, wherein the fitness program determining device is further configured to determine a group personalized dose of exercise for the group and individual personalized dose of exercise for each of the one or more subjects of the group based on the information of the one or more subjects.

7. The system of claim 6, wherein the computing device is configured to:
   obtain additional information for each subject of the one or more subjects during the personalized dose of exercise as performed by each subject; and
   send the additional information to the fitness program determining device,
   wherein the fitness program determining device stores the additional information.

8. The system of claim 7, wherein the fitness program determining device is also configured to modify the personalized dose of exercise being delivered to each subject in response to the additional information obtained during the personalized dose of exercise.

9. The system of claim 1, wherein the computing device is selected from the group consisting of: a mobile device, a desktop computer in communication, a laptop, a smart television, a smart phone, a tablet computer, a fitness tracker, historical information of the subject, a body composition analyzer, a personal monitoring device, a power output monitoring device connected to a piece of equipment in one or exercise zones, and combinations thereof,
   wherein the power output monitoring device and the computing device are in communication with the fitness program determining device.

10. The system of claim 9, wherein the fitness program determining device comprises a server, wherein the fitness program determining device is in communication with at least one of the instruction device and the computing device.

11. The system of claim 10, wherein
    the instruction device is configured to function in an offline mode when not connected to the fitness program determining device, wherein the instruction device shows its own selection of exercises from pre-stored plurality of exercises that is not-subject specific.

12. The system of claim 1, further comprising a reporting device configured to:
    receive personalized statistics information about the subject from one or more personal information capturing devices;
    create a smart report for the subject by measuring and/or interpreting the subject's analytics in relation to the subject's starting analytics and based on the personalized statistics information, information about the workouts, user inputs, inputs from the computing device, statistics derived from body scans of the subject, changing statistics measured during the workout according to the personalized dose of exercise and compared to the statistics prior to the workout and after the workout, and long-term fitness goal of the subject; and present a smart report to the subject, wherein the smart report is displayed on the computing device.

13. A method for delivering a personalized dose of exercise to one or more subjects, the method comprising:

obtaining, by a computing device, information pertaining to the one or more subjects;

determining, by a fitness program determining device, a personalized dose of exercise for a subject of the one or more subjects based on information of the subject received from the computing device and the pre-stored information related to exercises from a database;

storing, by the fitness program determining device, information pertaining to the one or more subjects;

scheduling, by the fitness program determining device, the personalized dose of exercise to one or more exercise zones and points in time in a physical gym comprising the one or more exercise zones; and providing, by an instruction device communicably coupled to both the fitness program determining device and the computing device, one or more personalized instructions to the subject based on the determined personalized dose of exercise at the points in time scheduled by the fitness program determining device, wherein the instruction device comprises an audio/video display device located in proximity to the one or more exercise zones, wherein, in each of the one or more exercise zones, a separate instruction device comprising a separate audio/video display device is installed, wherein the one or more personalized instructions comprises at least one of: instructions for performing one or more activities in at least one exercise zone of one or more exercise zones, an order in which the one or more activities to be performed in the one or more exercise zones, and a workout sequence and a timing in which the one or more exercise zones are to be completed to deliver the personalized dose of exercise for the subject, wherein the one or more subjects comprises two or more subjects, and wherein each of the one or more exercise zones accommodates the two or more subjects performing an activity simultaneously, wherein the instruction device is configured to provide instructions to the two or more subjects when the two or more subjects are in a same exercise zone of the one or more exercise zones, wherein the instructions simultaneously instruct the two or more subjects to perform a different personalized exercise activity.

14. The method of claim 13, wherein:

for each of the one or more subjects, the information is selected from the group consisting of: an age, a gender, a desired general fitness goal, a desired workout style for the dose of exercise, a desired target area for the dose of exercise, a desired time, date, duration of dose of exercise and/or location for the dose of exercise, historical information of the subject, a details of one or more previous doses of exercise delivered to the subject, data relating to a parameter selected from the group consisting of weight, heart rate, blood pressure, percentage body fat, BMI, blood glucose level, ECG, respiratory rate, muscle mass, steps, energy expenditure, energy intensity, and combinations thereof; and the personalized dose of exercise for the subject comprises at least one of a plurality of exercises to be performed by the subject in each of the one or more exercise zones.

15. The method of claim 14, further comprising:

determining, by the fitness program determining device, a personalized smart meal plan for the subject based on the information of the subject and the pre-stored information related to smart meal plans from the database.

16. The method of claim 14, wherein the subject is part of a group comprising the one or more subjects.

17. The method of claim 16, further comprising:

determining, by the fitness program determining device, a group personalized dose of exercise for the group and individual personalized dose of exercise for each of the one or more subjects of the group based on the information of the one or more subjects.

18. The method of claim 16, further comprising:

obtaining, by the computing device, additional information for each subject of the one or more subjects during the personalized dose of exercise as performed by each subject;

storing, by the fitness program determining device, the additional information; and modifying, by the fitness program determining device, the personalized dose of exercise being delivered to each subject in response to the additional information obtained during the personalized dose of exercise.

19. The method of claim 18, wherein:

the computing device is selected from the group consisting of: a mobile device, a desktop computer in communication, a laptop, a smart television, a smart phone, a tablet computer, a fitness tracker, a body composition analyzer, a personal monitoring device, a power output monitoring device connected to a piece of equipment in one or exercise zones, and combinations thereof, the power output monitoring device and the computing device are in communication with the fitness program determining device;

the fitness program determining device comprises a server, and the fitness program determining device is in communication with the instruction device and the computing device.

20. The method of claim 13, further comprising:

receiving, by a reporting device, personalized statistics information about the subject from one or more personal information capturing devices;

creating, by the reporting device, a smart report for the subject by measuring and/or interpreting the subject's analytics in relation to the subject's starting analytics and based on the personalized statistics information, information about the workouts, user inputs, inputs from the computing device, statistics derived from body scans of the subject, changing statistics measured during the workout according to the personalized dose of exercise and compared to the statistics prior to the workout and after the workout, and long-term fitness goal of the subject; and presenting, by the reporting device, a smart report to the subject, wherein the smart report is displayed on the computing device.

* * * * *